US00PP12949P2

(12) United States Plant Patent
Brown

(10) Patent No.: US PP12,949 P2
(45) Date of Patent: Sep. 10, 2002

(54) SALVIA PLANT NAMED 'SANTA BARBARA'

(76) Inventor: Kathiann Brown, 145 Vista de la Cumbre, Santa Barbara, CA (US) 93105

( * ) Notice: Subject to any disclaimer, the term of this patent is extended or adjusted under 35 U.S.C. 154(b) by 12 days.

(21) Appl. No.: 09/853,415

(22) Filed: May 11, 2001

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—Susan B. McCormick

(57) ABSTRACT

A new and distinct cultivar of Salvia named 'Santa Barbara' characterized by short height, compact habit, small gray-green leaves, short internodes, and flocculent dark purple flowers which appear violet in full sunlight and which are borne above the foliage on short racemes.

2 Drawing Sheets

BOTANICAL CLASSIFICATION

*Salvia leucantha.*

VARIETY DENOMINATION

'Santa Barbara'

BACKGROUND OF THE INVENTION

The present invention relates to a new and distinct cultivar of *Salvia leucantha*, hereinafter referred to by the cultivar name, 'Santa Barbara'. *Salvia leucantha* (unpatented) is a low-growing shrub found growing wild in Mexico and tropical Central America. *Salvia leucantha* 'Midnight' (unpatented) is a selection of *Salvia leucantha* which has a purple flower and a purple calyx. Both plants are grown and used widely in gardens and landscapes in California.

The inventor grew up in Santa Barbara, Calif., and has a keen interest in plants that are well suited to the Mediterranean climate of the region. For thirty-five years the inventor has pursued her horticultural interests by serving as a Master Gardener in both Minnesota and California, by maintaining and landscaping gardens for various clients, and by volunteering at the Santa Barbara Botanic Garden, a garden renowned for its living native plant collection and its study of plants native to California. The inventor thereby acquired the skill necessary to discern the variation displayed by 'Santa Barbara', to propagate and observe vegetative divisions of the invention, and to become satisfied by observation and research that the present invention is a new cultivar.

The inventor discovered 'Santa Barbara' growing approximately one meter from a plant of *Salvia leucantha* 'Midnight' (unpatented) in a cultivated area of Santa Barbara, Calif. The discovery was made in the spring of 1995. The soil in which these plants were growing was sandy and dry, conditions to which *Salvia leucantha* and the selection 'Midnight' are particularly well suited. The inventor observed that 'Santa Barbara' had smaller leaves, shorter internodes, and was not as tall as the adjacent and typical plant. When 'Santa Barbara' flowered in the spring of that year, it was observed that the flower spikes were also in proportion to the plant's smaller size. In summary, all the dimensions of 'Santa Barbara' were one half to two thirds the size of the adjacent 'Midnight'.

The inventor sought to locate similarly compact forms of *Salvia leucantha*, but has been unable to discover any *Salvia leucantha* or variety thereof which exhibits or approaches the degree of compactness of 'Santa Barbara'.

The inventor presumes that 'Santa Barbara' is a seedling of the adjacent plant, despite the low incidence of seedlings of *Salvia leucantha* or of *Salvia leucantha* 'Midnight' found in gardens and landscapes. Neither the inventor nor Dr. Dieter Wilken, Director of Research at the Santa Barbara Botanic Garden, has been able to find seed in 'Santa Barbara'. Dr. Wilken dissected several of the plant's "spent" flowers in January 2001, finding no seed, and in March of the same year, dissected several fresh flowers. Dr. Wilken found that the relative position of the stamens and pistils in 'Santa Barbara' would not hinder self-pollination (whereas self-pollination is difficult in some salvias whose stamens are strongly displaced from their pistils). Dr. Wilken concluded that 'Santa Barbara' may be either self-incompatible, i.e., genetically incapable of self-pollination, or is sterile, i.e., its pollen grains or ovules are sterile (as a result of several possible factors).

'Santa Barbara' has small gray-green leaves and dark purple flowers. The flowers appear violet in full sunlight. 'Santa Barbara' is not as tall as either *Salvia leucantha* or *Salvia leucantha* 'Midnight'. 'Santa Barbara' is further characterized by short flower stalks that are borne above the foliage, short internodes, and, overall, a consistently compact habit.

The inventor made the first asexual propagation in Santa Barbara, Calif., by division of the initial plant during the winter 1997/98. Subsequently, the plant was propagated from tip cuttings taken from the original specimen and from tip cuttings taken from divisions of the original specimen. At the present time many cycles of cutting propagation have been carried out by the inventor. The claimed distinguishing characteristics have remained stable and fixed throughout all cycles.

SUMMARY OF THE INVENTION

The following list represents the distinguishing characteristics of the new Salvia cultivar 'Santa Barabara' which, in combination, set 'Santa Barbara' apart from all other varieties of *Salvia leucantha* known to the inventor. 'Santa Barbara' has not been tested under all possible conditions.

Phenotypic differences might occur with variations in environmental, climatic, and cultural conditions without any variance in genotype.

1. The new cultivar 'Santa Barbara' is short in height.

2. The new cultivar 'Santa Barbara' exhibits a compact habit.

3. The new cultivar 'Santa Barbara' exhibits small gray-green leaves.

4. The new cultivar 'Santa Barbara' exhibits short internodes.

5. The new cultivar 'Santa Barbara' exhibits flowers that are dark purple and which appear violet in full sunlight.

6. The new cultivar 'Santa Barbara' exhibits short flower stalks that rise above the foliage.

BRIEF DESCRIPTION OF THE DRAWINGS

The accompanying color photographs illustrate the distinguishing traits of the new cultivar.

Sheet 1 shows the entire plant 'Santa Barbara' in bloom, from a side perspective.

Sheet 2 shows a specimen of 'Santa Barbara' (on the left) next to the presumed parent plant *Salvia leucantha* 'Midnight' (on the right). The prints were made using conventional photographic techniques and although flower and foliage colors in the photographs may differ from the actual colors due to light reflectance, they are as accurate as conventional photography can portray.

BOTANICAL DESCRIPTION OF THE PLANT

The following is a detailed botanical description of the new Salvia cultivar 'Santa Barbara'. Observations, measurements, color determinations, and comparisons were made in Arroyo Grande, Calif., from plants that were grown outdoors in one-gallon containers. Color determinations were made in accordance with The Royal Horticultural Society Colour Chart from London, England, except where general color terms of ordinary dictionary significance are used. The growing requirements of the new variety are similar to the species and there are no known growing problems.

Botanical classification: *Salvia leucantha* 'Santa Barbara'.
Common name: Mexican sage.
Parentage: Salvia 'Santa Barbara' is presumed to be a naturally occurring seedling of *Salvia leucantha* 'Midnight' (unpatented).
Propagation method: Propagation is accomplished by the methods of division and tip cuttings.
Rooting habit: Fine and fibrous.
Time to develop roots: Approximately 20 days are required to develop roots from an initial tip cutting.
Crop time: Six months are required to achieve a finished one-gallon container from an initial tip cutting.
Plant habit: Compact habit.
Use: Ornamental shrub.
Type: Perennial herb.
Growth rate: Moderate to vigorous.
Height of plant: At 2 years of age, and in bloom, 'Santa Barbara' is 90 cm. in height.
Width of plant: At 2 years of age, and in bloom, 'Santa Barbara' is 75 cm. in width. Hardiness: USDA Zone 9.

Stem:
- *Branching habit.*—Erect and ascending.
- *Stem color.*—Overall color effect is 144A suffused with 200A.
- *Stem shape.*—Terete.
- *Stem width.*—3 mm. in width.
- *Stem length* (*main stems*).—7 cm. in length.
- *Stem length* (*secondary stems*).—5 cm. in length.
- *Internode length.*—2–5 cm. between nodes.
- *Stem surface.*—Pubescent with flocculent patches.
- *Color of pubescence* (*and flocculence*).—156A.

Foliage:
- *Leaf arrangement.*—Opposite.
- *Leaf division.*—Simple.
- *Leaf shape.*—Linear to ovate.
- *Leaf length.*—5 cm. in length.
- *Leaf width.*—1 cm. in width.
- *Leaf tip.*—Acute.
- *Leaf base.*—Rounded.
- *Quantity of leaves.*—15 to 16 per stem.
- *Leaf venation pattern.*—Reticulate with prominent mid-vein protruding on lower surface and depressed on upper surface.
- *Vein color* (*adaxial surface*).—153A.
- *Vein color* (*abaxial surface*).—197C.
- *Margin type.*—Crenulate and pubescent.
- *Leaf surface* (*adaxial*).—Furrowed and pubescent.
- *Leaf surface* (*abaxial*).—Furrowed and flocculent.
- *Leaf attachment.*—Petiolate.
- *Petiole dimensions.*—3–6 mm. in length and 1 mm. in width.
- *Petiole surface.*—Flocculent.
- *Color of flocculence.*—156A.
- *Petiole color.*—192A.
- *Mature leaf color* (*adaxial*).—147B.
- *Mature leaf color* (*abaxial*).—A combination of 192A and 194A.
- *Young leaf color* (*adaxial*).—147B.
- *Young leaf color* (*abaxial*).—A combination of 192A and 194A.

Flower:
- *Bud shape.*—Pandurate.
- *Bud color.*—The overall color is 83B. In full sunlight the color is 81B.
- *Bud surface.*—Flocculent.
- *Color of flocculence.*—83B.
- *Bud dimensions.*—5 mm. in diameter and 9 mm. in length.
- *Shape of corolla tube.*—Tubular in shape.
- *Surface of corolla tube.*—Flocculent.
- *Corolla tube color.*—The overall color is 83B. In full sunlight the color is 81B.
- *Flower dimensions* (*calyx, corolla tube, and lobes*).—2 cm. in length and 5 mm. in diameter.
- *Number of corolla lobes.*—Two primary lobes and two reduced lateral lobes.
- *Shape of primary corolla lobes.*—Upper lobe falcate and lower lobe spreading.
- *Color of lobes.*—83B.
- *Number of petals.*—Two in number.
- *Color of petals.*—The overall color is 83B. In full sunlight the color is 81B.
- *Petals fused or unfused.*—Petals are basally fused.
- *Shape of petals.*—Spatulate.
- *Flowering season.*—Year round in Southern California and spring to summer in cooler regions of California.

*Aspect.*—Facing outward.
*Inflorescence form.*—Raceme.
*Flower arrangement.*—Flowers are arranged in whorls, as is typical of the species and its known cultivars.
*Quantity of flowers.*—A range of 7–9 flowers per whorl and a range of 9–18 whorls per raceme.
*Distance between whorls.*—1.5 cm. to 2.5 cm. between whorls.
*Peduncle dimensions.*—2.5 mm. in width by 16 cm. in length.
*Peduncle shape.*—Terete in shape.
*Peduncle surface.*—Flocculent surface.
*Color of flocculence* (*peduncle*).—156A.
*Peduncle color.*—Overall color is 138A combined with streaks of 187B.
*Calyx shape.*—Tubular-shaped.
*Calyx dimensions.*—9 mm. in length and 6 mm. in diameter.
*Calyx color* (*outer surface*).—The overall color is 83B. In full sunlight the color is 81B.
*Calyx surface* (*outer surface*).—Floccose.
*Calyx color* (*inner surface*).—138A.
*Calyx surface* (*inner surface*).—Pubescence absent. Surface rugose.
*Number of sepals.*—Two in number.
*Fused or unfused.*—Basally fused.
*Sepal color.*—The overall color is 83B. In full sunlight the color is 81B.

Reproductive organs:
*Pistil.*—One in number.
*Pistil shape.*—Filiform.
*Pistil dimensions.*—14 mm. in length and 0.50 mm. in width.
*Pistil color.*—155A.
*Pistil surface.*—Fimbriate.
*Color of fimbrillae* (*on pistil*).—155A.
*Stigma shape.*—Two-lobed with adaxial lobe involute and exhibiting fimbrillae.
*Stigma dimensions.*—0.50 mm. in width and 4 mm. in length, 3 mm. of which extend beyond the lobes of the flower petals.
*Stigma color.*—Stigma is 155A and the fimbrillae on stigma are 83B.
*Style shape.*—Filiform.
*Style dimensions.*—10 mm. in length and 3 mm. in width.
*Style color*—155A.
*Stamens.*—Two in number, included and fused at the base, creating a V-shape and anchored to the inside of corolla tube by bilateral appendages.
*Dimensions of stamens and appendages.*—The stamens are 6 mm. in length and 1 mm. in width. The appendages are 3 mm. in length and 1 mm. in width.
*Color of filament and appendages.*—155A.
*Anther dimensions.*—2.5 mm. in length and 1 mm. in width.
*Anther color.*—159A.
*Pollen color.*—162C.
*Pollen amount.*—Low to moderate.
*Ovary position.*—Superior.
*Ovary dimensions.*—3 mm. in height and 1.5 mm. in width.
*Ovary color.*—158A.

Seed: Assumed to be sterile. No seed has been observed by the inventor.

I claim:

1. A new and distinct variety of Salvia plant named 'Santa Barbara', as illustrated and described.

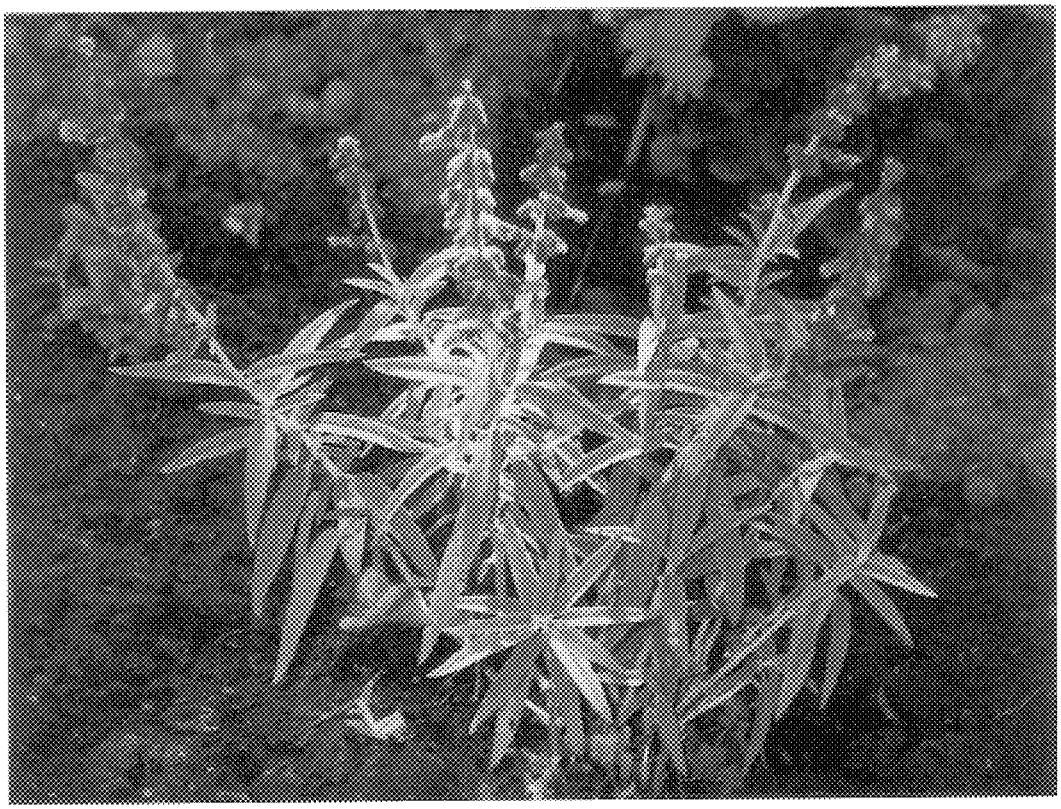

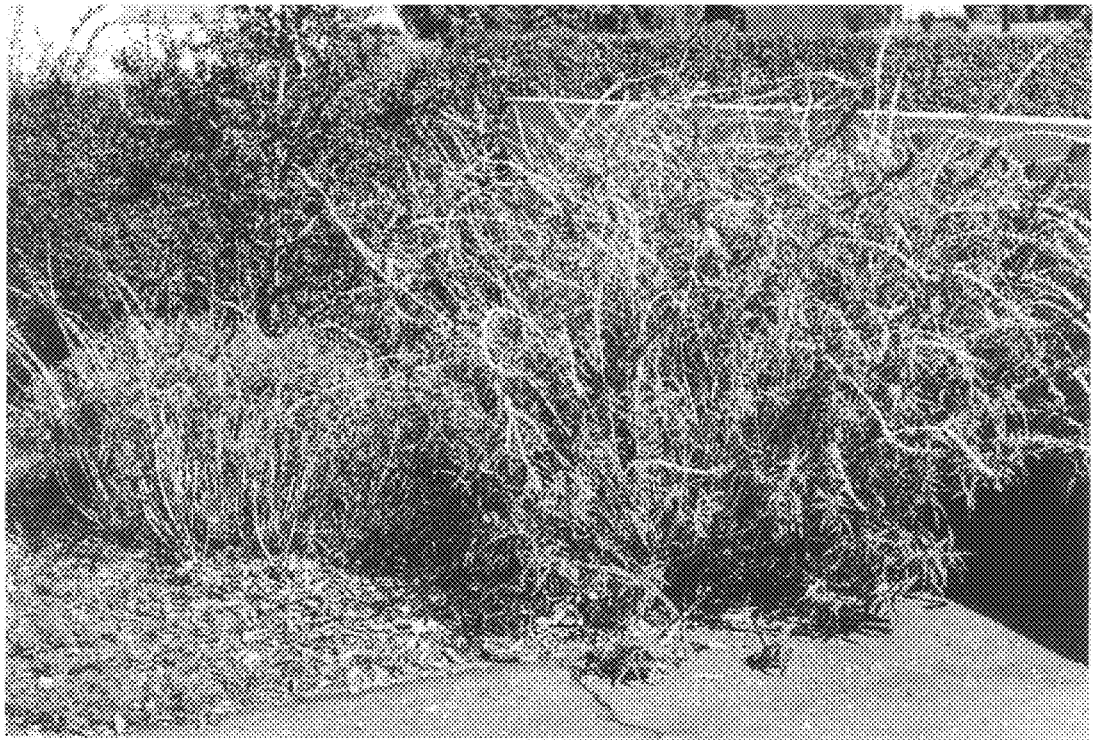

* * * * *